US010376564B2

(12) United States Patent
Klatzmann et al.

(10) Patent No.: US 10,376,564 B2
(45) Date of Patent: Aug. 13, 2019

(54) INTERLEUKIN-2 FOR TREATING FOOD ALLERGY

(71) Applicants: SORBONNE UNIVERSITE, Paris (FR); ASSISTANCE PUBLIQUE—HÔPITAUX DE PARIS, Paris (FR); CENTRE NATIONAL DE LA RECHERCHE SCIENTIFIQUE, Paris (FR)

(72) Inventors: David Klatzmann, Paris (FR); Bertrand Bellier, Paris (FR)

(73) Assignees: SORBONNE UNIVERSITE, Paris (FR); ASSISTANCE PUBLIQUE—HOPITAUX DE PARIS, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 84 days.

(21) Appl. No.: 15/124,734

(22) PCT Filed: Mar. 10, 2015

(86) PCT No.: PCT/EP2015/054991
§ 371 (c)(1),
(2) Date: Sep. 9, 2016

(87) PCT Pub. No.: WO2015/135956
PCT Pub. Date: Sep. 17, 2015

(65) Prior Publication Data
US 2017/0020962 A1 Jan. 26, 2017

(30) Foreign Application Priority Data
Mar. 11, 2014 (EP) .................... 14305348

(51) Int. Cl.
*A61K 38/16* (2006.01)
*A61K 38/20* (2006.01)
*A61K 9/00* (2006.01)
*A61K 39/35* (2006.01)
*A61K 39/00* (2006.01)

(52) U.S. Cl.
CPC ........ *A61K 38/2013* (2013.01); *A61K 9/0053* (2013.01); *A61K 38/20* (2013.01); *A61K 39/35* (2013.01); *A61K 2039/542* (2013.01); *A61K 2039/55533* (2013.01)

(58) Field of Classification Search
None
See application file for complete search history.

(56) References Cited

U.S. PATENT DOCUMENTS 5,989,546 A    11/1999  Lenardo

FOREIGN PATENT DOCUMENTS

WO    WO 2012/123381    9/2012
WO    WO 2013/184976    12/2013

OTHER PUBLICATIONS

Hershko, A.Y. et al. "Mast Cell Interleukin-2 Production Contributes to Suppression of Chronic Allergic Dermatitis" *Immunity*, Jul. 29, 2011, pp. 562-571, vol. 35, No. 4.
Moloney, M. et al. "Allergen-Specific Regulatory T Cells (Tregs) in Milk Allergic Children" Journal of Allergy and Clinical *Immunology*, Feb. 1, 2008, p. S261, #1012, vol. 121, No. 2.
Written Opinion in International Application No. PCT/EP2015/054991, dated Apr. 1, 2015, pp. 1-6.
Bonnet, B. et al. "Low-Dose IL-2 Induces Regulatory T Cell-Mediated Control of Experimental Food Allergy" *The Journal of Immunology*, 2016, pp. 188-198, vol. 197.
Brandt, E. B. et al. "Mast cells are required for experimental oral allergen-induced diarrhea" *J. Clin. Invest.*, 2003, vol. 112, pp. 1666-1677.
Littman, D. R. et al. "Th17 and Regulatory T Cells in Mediating and Restraining Inflammation" *Cell*, Mar. 19, 2010, pp. 845-858, vol. 140.
Passalacqua, G. et al. "Current insights in allergen immunotherapy" *Ann Allergy Asthma Immunol*, 2018, pp. 152-154, vol. 120.
Sampson, H. A. et al. "Mechanisms of food allergy" *J Allergy Clin Immunol.*, 2018, pp. 11-19, vol. 141, No. 1.
Schwartz, R. H. "T Cell Anergy" *Annu. Rev. Immunol.*, 2003, pp. 305-334, vol. 21. Contents pp. 1-2.
Silva, E. Z. M. DA. et al. "Mast Cell Function: A New Vision of an Old Cell" *Journal of Histochemistry & Cytochemistry*, 2014, pp. 698-738, vol. 62, No. 10.
Simons, F. E. R. "Anaphylaxis: Recent advances in assessment and treatment" *J Allergy Clin Immunol*, Oct. 2009, pp. 625-636, vol. 124.

*Primary Examiner* — Shulamith H Shafer
(74) *Attorney, Agent, or Firm* — Saliwanchik, Lloyd & Eisenschenk

(57) ABSTRACT

The present invention relates to the use of interleukin-2 (IL-2) for treating a food allergy, either by inducing non-specific tolerance against food allergens, or in a desensitization protocol in combination with a food allergen.

19 Claims, 5 Drawing Sheets

A

B

Figure 5:
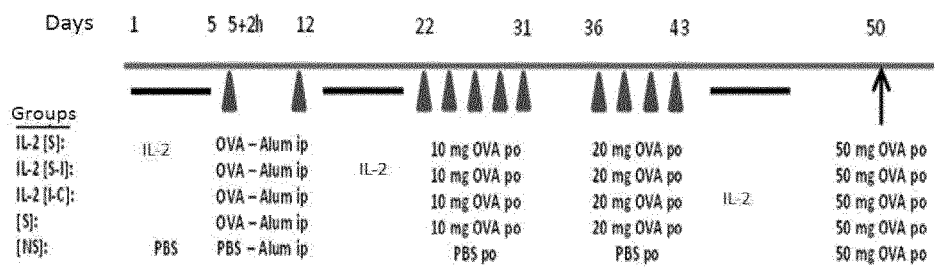
Figure 5:
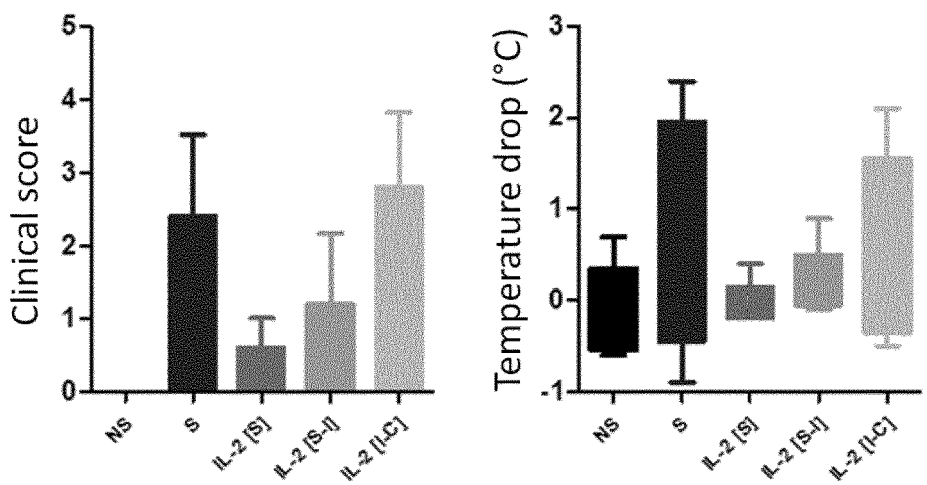

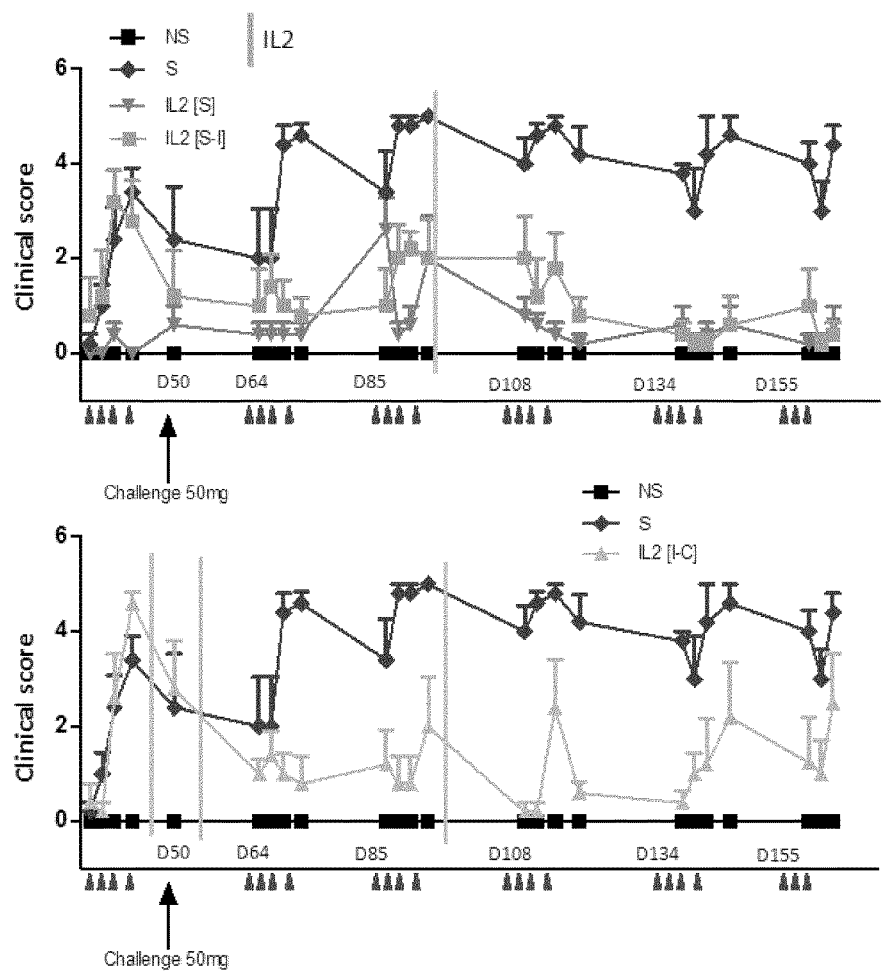
Figure 5 (continuation)

INTERLEUKIN-2 FOR TREATING FOOD ALLERGY

CROSS-REFERENCE TO RELATED APPLICATION

This application is the U.S. national stage application of International Patent Application No. PCT/EP2015/054991, filed Mar. 10, 2015.

The present invention relates to the treatment of food allergies.

BACKGROUND OF THE INVENTION

Food allergies are a growing health concern with dramatic increase in the last two decades. More than 12 million US Americans suffer from food allergies. The incidence of food allergy is highest in young and decreases with age.

Allergic responses caused by food allergy can range from mild responses, such as dermatitis, gastrointestinal and respiratory distress, to severe reactions, such as anaphylaxis, including biphasic anaphylaxis and vasodilation. Anaphylaxis is a life threatening systemic condition, causing a constriction of the trachea, preventing breathing, and anaphylactic shock. Peanuts and tree nuts account for the majority of the life-threatening and fatal reactions.

Food-induced allergic reactions result from immunological pathways that include activation of effector cells through food specific IgE antibodies, cell-mediated (non-IgE-mediated) reactions resulting in subacute or chronic inflammation, and the combination of these pathways. Several studies investigating pathogenesis of food allergy point to a functional role for regulatory T lymphocytes (Treg) in the development of normal tolerance to food allergens and the spontaneous resolution of milk allergy (Karlsson M R, Rugtveit J, Brandtzaeg P. J Exp Med 199(12), 1679-1688 (2004), Sletten G B, Halvorsen R, Egaas E, Halstensen T S. International archives of allergy and immunology 142(3), 190-198 (2007)). Oral immune tolerance is indeed dependent on the induction of allergen-specific Treg cells that block the generation of allergen-specific IgE. In patients with food allergy, oral immunotherapy has been reported to be associated with changes in various immune parameters, including a boosting of levels of IgG4 and IgA, reduction in basophil and mast cell reactivity; and changes in Treg cell or T effector cell numbers. Development of milk-specific Tregs in milk allergic subjects ultimately led to tolerance, indicating that Tregs may be a driving force in outgrowth of milk allergy (Shreffler, et al. J. Allergy Clin. Immunol., 123 (2009), pp. 43-52).

There is no treatment commercially available to treat a food allergy. The current standard of care is strict avoidance of the offending allergens and immediate access to rescue medications, such as epinephrine and antihistamines. Indeed, the great majority of allergic patients are treated by symptomatic medication using drugs that, for example, prevent the degranulation of mast cells, exhibit general anti-inflammatory activity and/or reverse bronchoconstriction or vasodilatation. However, symptomatic medication fails to target the mechanisms underlying allergic disease, and often has only short activity.

There is a need for an effective long-term treatment and protection against food allergies.

SUMMARY OF THE INVENTION

It is herein described a method for treating a food allergy in a subject, which method comprises administering the subject with interleukin-2 (IL-2).

The present invention relates to the use of IL-2 for treating a food allergy, either by inducing non-specific tolerance against food allergens, or in a desensitization protocol, in combination with a food allergen.

IL-2 is advantageously administered at a dosage, which effectively activates Tregs without substantially activating Teffs. The consequence is a dramatic increase in the Treg/Teff balance in the subject, without impact on its immunocompetency.

According to a particular aspect, IL-2 may be administered repeatedly, e.g. during a cyclic period which lasts from about 1 month to about one year, which cyclic period may be repeated every two or three years, whereby the subject becomes tolerant to the allergens.

IL-2 is particularly useful for reducing the risk or severity of an allergic response or crisis.

According to another aspect, IL-2 may be administered in combination with a food allergen which is at a dosage suitable for desensitizing the subject against said food allergen.

Interleukin-2 (IL-2) may be administered by any convenient route, including oral, buccal, sublingual, subcutaneous, intranasal, or intrarectal route.

In a preferred embodiment, IL-2 is administered orally and at a dosage between 0.5 and 50 MIU/day, 1 and 40 MIU/day, preferably 3 to 30 MIU/day, still preferably 5 to 10 MIU/day.

LEGEND TO THE FIGURES

Figure 1:
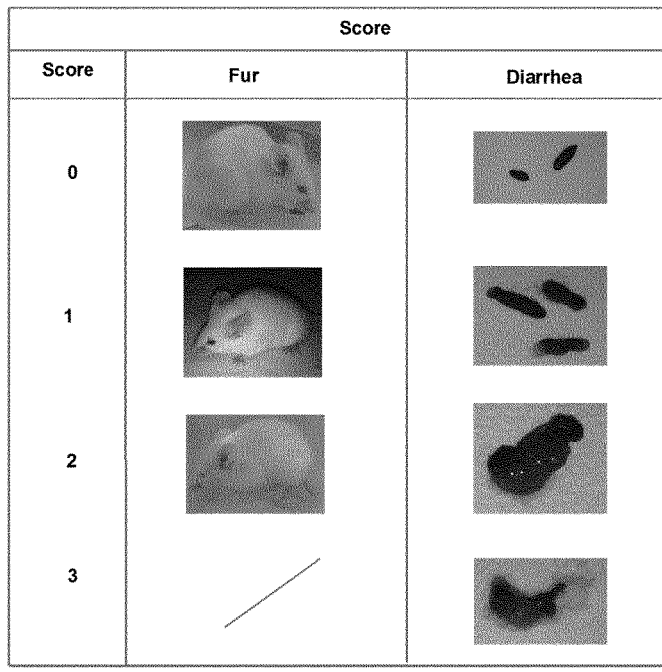

FIG. 1: Criterion for scoring.

Allergic diarrhea was assessed by a severity score of fecal form from 0 to 3: score 0, solid state; score 1, funicular form; score 2, slurry; score 3, watery state and ruffled aspect of the fur (score 0, 1, 2).

Figure 2:
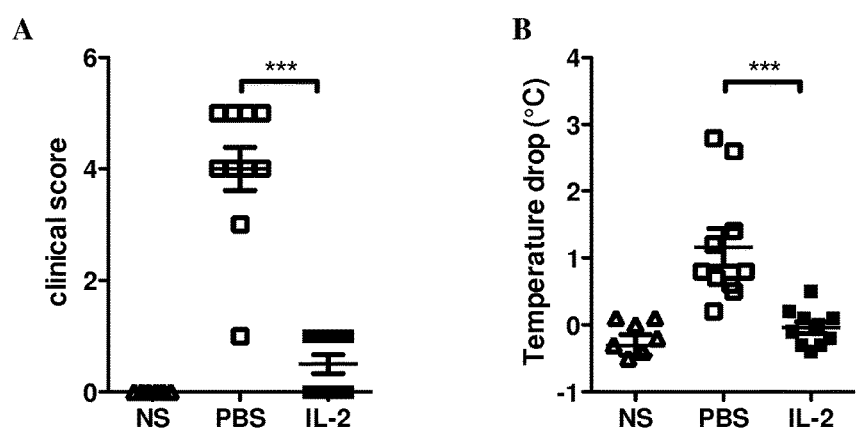

FIG. 2: Preventive treatment with low-dose IL-2 prevented the allergic diarrhea and the drop of body temperature.

Mice were i.p. treated with low-dose IL-2 or PBS during 5 days and then sensitized with OVA/Alum and orally treated with OVA to induce food allergy. Controls (NS) are untreated and unsensitized mice. Food allergy was estimated by (A) clinical score and (B) changes in body temperature.

Figure 3:
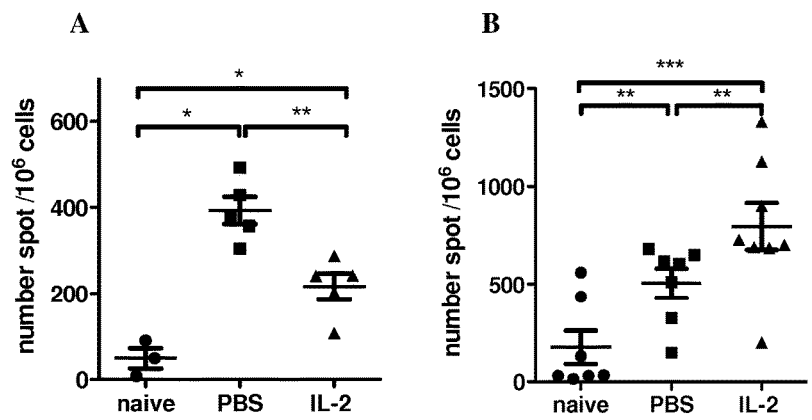

FIG. 3: OVA-specific immune responses.

After OVA challenges, cells of IL-2 treated or untreated mice were isolated from Peyer's patches (A) or mesenteric LN (B) and restimulated with OVA during 24 hours in an IL-4 (A) and IFNg (B) specific ELISpot. Data from individual mice (n=5 to 8 per group) and mean±SEM values are shown (horizontal lines).

Figure 4:
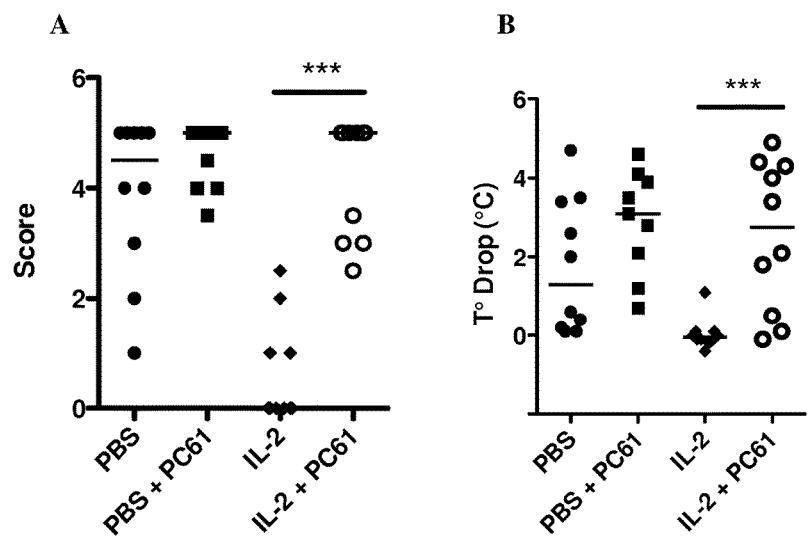

FIG. 4: Treg depletion abrogates low-dose IL-2 treatment efficacy.

Mice were treated with low dose IL-2 or PBS and injected with PC61 mAb that induces CD25-expressing Treg depletion. Mice were then sensitized with OVA as previously and challenged p.o. with OVA to induce food allergy. Allergy symptoms (A) and body temperature variations (B) were measured one hour after the $5^{th}$ challenges. Data from individual mice (n=8 to 10 per group) and median (horizontal lines) values are shown.

FIG. 5: Preventive and therapeutic administrations of low-dose IL-2 induce long-term immune protection against food allergy.

OVA-sensitized mice were i.p. treated with low-dose IL-2 or PBS (S) during 5 days before ([S-I]) or after ([I-C]) the allergic induction phase. Controls (S) are untreated sensitized mice. Food allergy was estimated by clinical score and changes in body temperature 1 h after a challenge with 50 mg of OVA (B) or after several gavages with 10 m of OVA (C).

Figure 6:
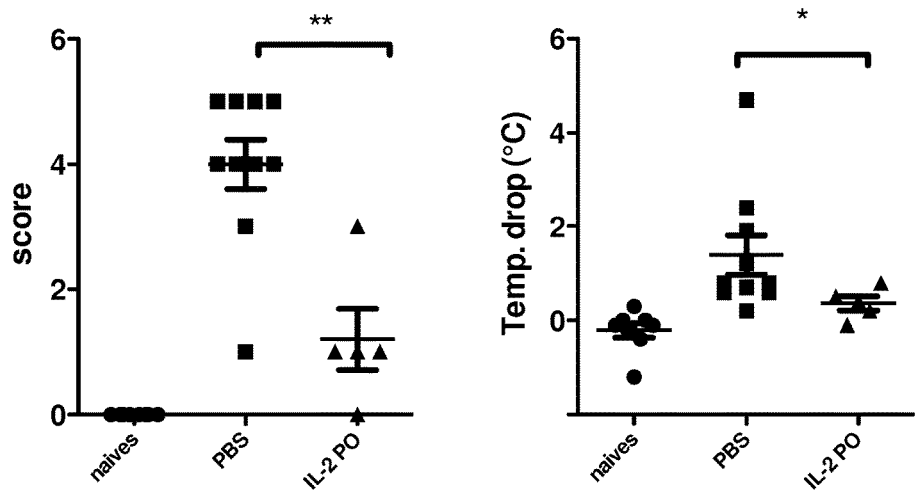

FIG. 6: Low-dose oral IL-2 treatment

Mice were treated with low dose IL-2 by oral (P.O.) route during 5 days. Mice were then sensitized with OVA as previously and challenged p.o. with OVA to induce food allergy. Allergy symptoms (A) and body temperature variations (B) were measured one hour after the 5$^{th}$ challenges. Data from individual mice (n=5 per group) and median (horizontal lines) values are shown.

Figure 7:
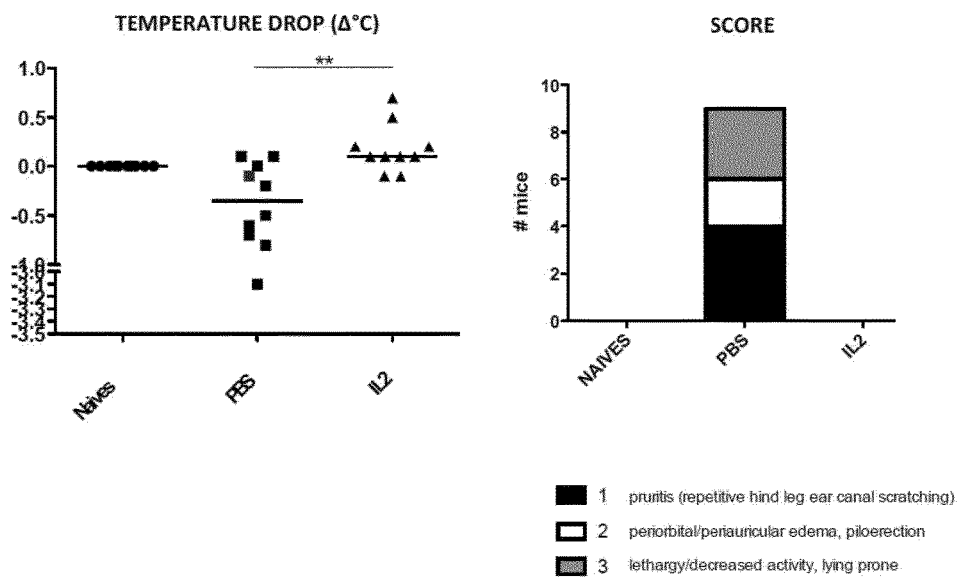

FIG. 7: Low-dose IL2 provides protection against clinical manifestations of peanut-specific food allergy.

Mice were treated during 5 days with low dose IL2 (IL-2; 50,000 IU/injection) or PBS (S) and then sensitized twice with 500 µg peanut extract (PE) proteins in alum and then challenged 6 times by oral PE administration (20 mg/challenge). In control, non-sensitized mice (naive) are included and challenged with PE. Body temperature variations and clinical scores, measured in the next hour following the challenge, are shown. Each dot represents individual value for each mouse and group means are shown (n=10 per group; **$P<0.01$, Mann Withney T test).

DETAILED DESCRIPTION OF THE INVENTION

Definitions

"Food allergy" is an adverse response to food triggered by an immunological reaction to a substance ingested in food. In other words, a food allergy is an allergy wherein the allergen is a food component. In particular, a food protein, a food protein fragment or a food protein fraction may act as an allergen in food allergies. A food allergy should be distinguished from non-immune-mediated adverse responses to food, such as food intolerance, pharmacological reactions and toxin-mediated reactions.

An "allergen" as used herein refers to one molecule or a combination of molecules capable of provoking an immune response in a subject, in particular the production of an antibody against the molecule, typically immunoglobulin E (IgE). An immune response where IgE is produced may be referred to as a type I hypersensitive response.

The "subject" to be treated may be an animal such as a mammal. Preferably, the subject to be treated is human. The subject may be an infant, a child, an adult or an elder.

The term "treating" or "treatment" means any improvement in the allergy. It includes alleviating at least one symptom, or reducing the risk, occurrence or severity of allergic response or crisis. In a particular embodiment, it includes desensitizing the subject, achieving long-term specific tolerance to a particular food allergen. Food allergy symptoms usually develop within a few minutes to two hours after eating the offending food.

The most common food allergy crisis includes any of the following signs or symptoms, alone or in combination:
- Tingling or itching in the mouth
- Hives, itching or eczema
- Swelling of the lips, face, tongue and throat or other parts of the body
- Wheezing, nasal congestion or trouble breathing
- Abdominal pain, diarrhea, nausea or vomiting
- Dizziness, lightheadedness or fainting In some people, a food allergy can trigger a severe allergic reaction called anaphylaxis. This can cause life-threatening signs and symptoms, including:
- Constriction and tightening of airways
- A swollen throat or the sensation of a lump in your throat that makes it difficult to breathe
- Shock with a severe drop in blood pressure
- Rapid pulse
- Dizziness, lightheadedness or loss of consciousness "Regulatory T cells" or "Tregs" are T lymphocytes having immunosuppressive activity. Natural Tregs are characterized as CD4+CD25+Foxp3+ cells. Tregs play a major role in the control of inflammatory diseases, although their mode of action in such diseases is not well understood. In fact, in most inflammatory diseases, Treg depletion exacerbates disease while Treg addition decreases it. Most Tregs are CD4+ cells, although there also exists a rare population of CD8+Foxp3+T lymphocytes with a suppressive activity.

Within the context of this application, "effector T cells" (or "Teff") designates conventional T lymphocytes other than Tregs (sometimes also referred to as Tconv in the literature), which express one or more T cell receptor (TCR) and perform effector functions (e.g., cytotoxic activity, cytokine secretion, anti-self recognition, etc). Major populations of human Teff according to this invention include CD4+T helper lymphocytes (e.g., Th0, Th1, Th17) and CD4+ or CD8+ cytotoxic T lymphocytes, and they can be specific for self or non-self antigens.

Food Allergy

An allergic response to a food antigen can be thought of as an aberrant mucosal immune response to an otherwise harmless antigen. The current view of mucosal immunity is that it is the antithesis of a typical systemic immune response. Contrary to the relatively antigen pristine environment of the systemic immune system, the micro- and macro-environment of the gastrointestinal (GI) tract is continuously exposed to commensal bacteria in the mouth, stomach, and colon and dietary substances (proteins, carbohydrates, and lipids) that, if injected subcutaneously, would surely elicit a systemic response.

The digestive tract's immune system is often referred to as gut-associated lymphoid tissue (GALT) and works to protect the body from invasion. GALT can be divided into induction sites, which consist of Peyer's patches (PP), isolated lymphoid follicles (ILF) and mesenteric lymph nodes (MLN) and effector sites, which consist of lymphocytes scattered throughout the epithelium and lamina propria. Dietary antigens may access the mucosal immune system by means of three different cell types: i) antigens can cross the intestinal epithelial cells (IEC) through different transcellular routes, ii) antigens can be sampled by dendritic cells (DC) that extend processes through the epithelium and into the lumen, or iii) antigens can be taken up by microfold (M) cells overlying PPs and ILFs (Brandtzaeg, P. Nat. Rev. Gastroenterol. Hepatol. 2010, 7:380-400).

The immunological mechanisms involved in the immune oral tolerance or the sensitization of individuals toward food components remain poorly understood but it is thought that allergens or digestive products must cross the intestinal mucosa in order to interact with the GALT, the same prerequisite thought for an allergen to elicit an allergic reaction in individuals already sensitized.

The adaptive immune response to food antigens in patients with food allergy is characterized by food-specific IgE production from B cells and a Th2-skewed T-cell response that drives the IgE class-switching.

Predisposition to food allergy involves a complex interaction between several genes and environmental factors, including chemokines. Specific chemokines (CCL2 and CCL11) were more elevated in food allergic children suffering from anaphylaxis than bronchial asthma and atopic dermatitis (Radman M et al. Inflammation, 2013, 36(3):561-6) suggesting specific immune regulation mechanisms.

Although there is a broad variety of known food allergens, over 90 percent of adverse food reactions are caused by food components in the following foods: milk, eggs, peanuts, tree nuts, wheat, soy, fish, and shellfish. Other examples of food allergies are allergies caused by food components in legumes (soy, peas, beans), corn, maize, fruits, vegetables, spices, synthetic and natural colors, chicken and chemical additives.

One of the most common food allergies is peanut allergy. Peanuts belong to the family of legumes (Fabaceae). Proteins in tree nuts, including pecans, almonds, cashews, pistachios, pine nuts, and walnuts, are another widespread allergen. Subjects suffering from tree nut allergy may be sensitive to one, or many, tree nuts. Furthermore, seeds, including sesame seeds and poppy seeds, may contain oils comprising a protein that can act as an allergen.

In particular embodiments, the food allergy may be thus selected from the group consisting of peanut allergy, milk allergy, nut allergy, corn allergy, fruit allergy, garlic allergy, oat allergy, shellfish allergy, soy allergy, wheat allergy (in particular gluten allergy), egg allergy, sesame allergy, olive oil allergy, cheese allergy, crustacean allergy, and fish allergy. Milk allergy may be further distinguished by the animal (cow, goat, etc.) from which the milk originates.

Food allergies include immediate (IgE mediated) food allergies, and (IgE/non-IgE and non IgE mediated) delayed food allergies. Immediate (IgE mediated food) allergy can affect many systems of the body (skin, gut, airway and circulation) and symptoms develop rapidly (within one hour of eating the food). In contrast, delayed forms of food allergy mainly affect the bowel and the skin and symptoms develop hours after eating the food. The immune mechanisms causing delayed food allergy are less well understood than IgE-mediated food allergy. The most common causative foods for delayed food allergies are cow's milk and soy. Unlike IgE mediated food allergy, delayed food allergies are very rarely life threatening. The present invention encompasses treating an immediate food allergy, or a delayed food allergy.

Interleukin-2 (IL-2)

Within the context of this invention, the term "IL-2" designates any source of IL-2, including mammalian sources such as human, mouse, rat, primate, and pig, and may be native or obtained by recombinant or synthetic techniques, including recombinant IL-2 polypeptides produced by microbial hosts. IL-2 may be or comprise the native polypeptide sequence, or can be an active variant of the native IL-2 polypeptide. Preferably, the IL-2 polypeptide or active variant is derived from a human source, and includes recombinant human IL-2, particularly recombinant human IL-2 produced by microbial hosts.

Active variants of IL-2 have been disclosed in the literature. Variants of the native IL-2 can be fragments, analogues, and derivatives thereof. By "fragment" is intended a polypeptide comprising only a part of the intact polypeptide sequence. An "analogue" designates a polypeptide comprising the native polypeptide sequence with one or more amino acid substitutions, insertions, or deletions. Muteins and pseudopeptides are specific examples of analogues. "Derivatives" include any modified native IL-2 polypeptide or fragment or analogue thereof, such as glycosylated, phosphorylated, fused to another polypeptide or molecule, polymerized, etc., or through chemical or enzymatic modification or addition to improve the properties of IL-2 (e.g., stability, specificity, etc.). Active variants of a reference IL-2 polypeptide generally have at least 75%, preferably at least 85%, more preferably at least 90% amino acid sequence identity to the amino acid sequence of the reference IL-2 polypeptide.

Methods for determining whether a variant IL-2 polypeptide is active are available in the art and are specifically described in the present invention. An active variant is, most preferably, a variant that activates Tregs.

Examples of IL-2 variants are disclosed, for instance, in EP109748, EP136489, U.S. Pat. No. 4,752,585, EP200280, and EP118,617.

Preferably, a recombinant IL-2 is used, i.e., an IL-2 that has been prepared by recombinant DNA techniques. The host organism used to express a recombinant DNA encoding IL-2 may be prokaryotic (a bacterium such as *E. coli*) or eukaryotic (e.g., a yeast, fungus, plant or mammalian cell). Processes for producing IL-2 have been described e.g., in U.S. Pat. Nos. 4,656,132, 4,748,234, 4,530,787, and 4,748,234, incorporated herein by reference.

In a preferred embodiment, the invention uses an IL-2 of human origin, or an active variant thereof, more preferably produced recombinantly. A nucleotide and an amino acid sequence of human IL-2 are disclosed, for instance, in Genbank ref 3558 or P60568, respectively. The invention more preferably uses a human IL-2.

IL-2 for use in the present invention shall be in essentially pure form, e.g., at a purity of 95% or more, further preferably 96, 97, 98 or 99% pure.

For use in the present invention, IL-2 is typically not combined or co-administered with a Teff suppressive agent. However, although not preferred or required, drug combinations may be contemplated.

IL-2 may be used in monomeric or multimeric form.

IL-2 is commercially available, including for pharmaceutical uses, and it is authorized for use in human patients. Suitable commercial forms include, e.g., Proleukin®, a recombinant human IL-2 composition,
Aldesleukin®, an unglycosylated des-alanyl-1, serine-125 human interleukin-2 produced in *E. coli*. and
Roncoleukin®, recombinant human IL-2 produced in yeast.

Interleukin-2 may be used alone or in combination with any other therapeutically active agent.

Dosage and Regimen

For use in the present invention, IL-2 is administered at a dosage, which effectively activates Tregs without substantially activating Teffs. The consequence is a dramatic increase in the Treg/Teff balance in the subject.

The induction (or activation or expansion) of Tregs can be measured, e.g., by measuring the number of Tregs (e.g., based on the expression of CD25, FoxP3) and/or the activity of Tregs in samples from the treated subject. The absence of substantial induction (or activation or expansion) of Teff can also be measured as disclosed in the examples, e.g., by measuring the number of Teff and/or the activity of Teff in samples from the treated subject. Preferably, the absence of substantial induction indicates the target Teff cell population does not acquire markers of activation such as CD25, CD69, and/or HLA-DR, or as assessed by whole transcriptome analyses. Detailed methods for detecting, measuring and quantifying Treg and Teff cells are well known per se in the art and some are disclosed in the examples.

Stimulation in Tregs may be measured by an increase in Treg counts in the patient, typically by 10% at least, or by an increase in activation markers such as the intensity of CD25 expression. The absence of Teff induction typically designates that the Teff cell population has not increased by more than 10% in said subject as a result of treatment.

The stimulation of Treg and absence of substantial induction of Teff is preferably assessed by a measurement of the ratio or the balance Treg/Teff in the treated subject.

Furthermore, the invention shows an increase not only in CD4+ Tregs, but also in a rare population of Tregs which are CD8+.

IL-2 is preferably used at a dosage which substantially avoids side effects, while very substantially inducing Tregs.

The effective dosage can be adjusted by the practitioner, based on information contained in the present application, and depending on the route of administration.

Typically the desired dosage, which is a functional dose that effectively activates Tregs without substantially activating Teffs, will be a low dosage if administered by the subcutaneous route, while it will be higher if administered by the oral route. Dosages suitable for routes of administration, such as the oral or intranasal routes, are thus adjusted so that they activate Tregs without substantially activating Teffs.

Generally speaking, IL-2 may be administered at a functional dose of D/10 to 20×D, preferably D/5 to 10×D, wherein D is the minimal dose triggering induction of expression of CD25 in Treg, without inducing expansion of Treg.

The amount of IL-2 to administer thus preferably depends on the body surface area of the subject. The body surface area (BSA) is the measured or calculated surface of a human body.

Various calculations have been published to arrive at the BSA without direct measurement:

The Dubois & Dubois formula (Dubois & Dubois Arch Intern Med 1916, 17:863) is commonly used in adults:

$$BSA(m^2) = 0.007184 \times weight\ (kg)^{0.425} \times height\ (cm)^{0.725} = \frac{weight\ (kg)^{0.425} \times height\ (cm)^{0.725}}{139.2}$$

Another commonly used formula is the Mosteller formula (Mosteller R D. "Simplified calculation of body-surface area". N Engl J Med 1987; 317:1098) adopted for use by the Pharmacy and Therapeutics Committee of the Cross Cancer Institute, Edmonton, Alberta, Canada:

$$BSA(m^2) = \sqrt{\frac{weight\ (kg) \times height\ (cm)}{3600}} = \frac{weight\ (kg)^{0.5} \times height\ (cm)^{0.5}}{60}$$

It is more particularly used in children.

Average BSA is generally taken to be 1.73 m² for an adult.

| Average BSA values | |
|---|---|
| Neonate (Newborn) | 0.25 m² |
| Child 2 years | 0.5 m² |
| Child 9 years | 1.07 m² |
| Child 10 years | 1.14 m² |
| Child 12-13 years | 1.33 m² |
| For men | 1.9 m² |
| For women | 1.6 m² |

A typical dosage is a dose of about 0.05 to about 20 MIU/m²/day, preferably 0.2 to about 10 MIU/m²/day, still preferably 0.5 to 5 MIU/m²/day.

Generally speaking, IL-2 may be administered at a dosage ranging from 0.05 MIU/day to 50 MIU/day.

In a preferred embodiment, particularly advantageous for subcutaneous administration, IL-2 is administered at a dose of less than about 5, preferably less than 3.5 MIU/day, preferably at a dose of between about 0.05 MIU and about 2 MIU/day, still preferably at a dose of between about 0.3 MIU/day and about 1 MIU/day, or between 0.1 to 3 MIU/day, preferably 0.1 to 1.5 MIU/day, still preferably 0.25 to 1 MUI/day.

Oral administration may benefit a dosage as high as 50 MIU/day for instance. In a preferred embodiment, IL-2 is administered orally at a dosage between 0.5 and 50 MIU/day, 1 and 40 MIU/day, preferably 3 to 30 MIU/day, still preferably 5 to 10 MIU/day.

Intranasal administration may benefit a dosage between 0.5 and 20 MIU/day, preferably 1 to 5 MIU/day.

Repeated daily dosing is contemplated, preferably from one month to about a year, preferably from three to six months, optionally every two or three years.

In a particular embodiment, IL-2 is used in a desensitization protocol. This involves administering increasing doses of food allergens to induce specific long-term tolerance. Preferably the allergens may be in the form of recombinant proteins. Allergens can be administered preferably by oral, sublingual or subcutaneous routes, in combination with IL-2 administration. The term "combination" means simultaneous, separate, or sequential administrations.

Administration Forms and Routes

Il-2 may be administered using any convenient route, including parenteral, e.g. subcutaneous, or intranasal routes. Oral administration is preferred. Liquid formulations, or solid formulations, including tablets or capsules, may be prepared for that prospect. Sublingual or buccal administrations are also encompassed.

IL-2 is typically administered in association (e.g., in solution, suspension, or admixture) with a pharmaceutically acceptable vehicle, carrier or excipient. Suitable excipients include any isotonic solution, saline solution, buffered solution, slow release formulation, etc. Liquid, lyophilized, or spray-dried compositions comprising IL-2 or variants thereof are known in the art and may be prepared as aqueous or nonaqueous solutions or suspensions. Preferably the pharmaceutical compositions comprise appropriate stabilizing agents, buffering agents, bulking agents, or combinations.

The Figures and Examples illustrate the invention without limiting its scope.

EXAMPLES

Example 1: IL-2 as Preventive Treatment of Food Allergy

Materials and Methods

The inventors have developed a murine food allergy model with high degree of anaphylaxis and allergic diarrhea induced by orally administered ovalbumin (OVA), 4 times during the 3rd week in pre-immunized mice.

Female BALB/c mice were sensitized with two intraperitoneal (i.p.) injections of 10 μgOVA mixed with aluminum hydroxide gel (alum) each over a span of 1 week. All the mice were orally administered OVA at a dose of 20 mg/mouse dissolved in phosphate-buffered saline (PBS, p.o.) four times a week to induce food allergy. Four to six oral treatments with OVA were required to induce severe allergic symptoms in untreated sensitized control mice.

Food allergy was evaluated by changes in fur aspect and by allergic diarrhea (FIG. 1). Allergic diarrhea was assessed by a severity score of fecal form from 0 to 3: score 0, solid state; score 1, funicular form; score 2, slurry; score 3, watery state. Fecal conditions with scores of 2 and 3 were defined as diarrhea. Criterion for scoring is shown in FIG. 1. Allergic symptoms were confirmed by loss in rectal temperature for 1 h after challenge. A gradual decrease in body temperature and an increase in diarrhea were induced in OVA-sensitized mice (not shown).

Results

The inventors confirmed that tolerance induction is obtained in mice orally pretreated with OVA before sensitization, then preventing the allergic diarrhea and inhibiting the production of OVA-specific IgE antibodies (data not shown).

They observed that a 5-day preventive treatment with low-dose IL-2 before sensitization fully protects mice from food allergy induction (FIG. 2).

The inventors evaluated the OVA-specific immune responses in these mice. They observed a reduction of IL-4 secreting cell number in Peyer's patches and an increase of IFNg secreting cell number in mesenteric lymph nodes in IL-2 treated mice compared to controls (FIG. 3), demonstrating that low-dose IL-2 has modulated the Th2/Th1 balance.

Example 2: Role of Treg in IL-2 Immunotherapy

To evaluate the role of Tregs in low-dose IL-2 treatment efficacy, the inventors performed similar experiments in which Tregs were depleted in IL-2 treated and control groups. Thus, mice were first treated with low dose IL-2 or PBS and then injected or not with PC61 mAb (anti-murine CD25 rat IgG1) to deplete CD25-expressing Treg. Mice were then sensitized and challenged with OVA to induce food allergy. The inventors observed that Treg depletion abrogates the efficacy of low dose IL-2 treatment since mice treated with PC61 had severe allergic symptoms and an important decrease in body temperature (FIG. 4).

Example 3: IL-2 Treatment Modalities 3.1. The inventors have further investigated the efficacy of IL-2 when administered after mice sensitization (late preventive effect) or allergy induction (therapeutic effect) and tested the long-term efficacy of the treatment (FIG. 5).

Mice were sensitized and treated with low-dose of IL-2 before the challenge ("IL-2 [S-I]": preventive treatment) or after the challenge ("IL-2 [I-C]": therapeutic treatment) with OVA. Several cycles of allergen administration were done to investigate the long-term efficacy of the treatment. In controls, mice were also treated before the sensitization ("IL-2 [S]" or non-treated (S)).

The inventors demonstrated that mice treated with IL-2 before the allergy induction ("IL-2 [S]" and "IL-2 [S-I]") or after allergy induction ("IL-2 [I-C]") are protected from allergic disease. The long-term efficacy of the preventive and therapeutic treatment has been proven since IL-2 treated are protected after several cycles of OVA administration. The inventors also observed that additional cure of IL-2 can improve the long-term efficacy of the treatment.

3.2. Preventive treatments of low-dose IL-2 were performed at the same doses using oral route of administration. Mice treated by oral routes were protected against OVA challenges as demonstrated by the reduction of allergic symptoms and the low variations of body temperature (FIG. 6). These results demonstrate that IL-2 can be used in p.o. treatment for food allergy.

Example 4: Peanut Allergy Model

Materials and Methods

A peanut allergy model was established by repeated oral administration of peanut extract (PE) proteins in sensitized mice. For that purpose, 7 week old BALB/C (AnNR/J) female mice were sensitized twice at one week interval by i.p. injection of 500 µg of Peanut-extract (PE) proteins mixed with 500 µg aluminium hydroxide gel (Alum, $AlH_3O_3$, Sigma) or PBS mixed with Alum as control (naive). Allergy was then induced 10 days later by PE oral administrations (20 mg/mouse), 6 times within a 2-week period. Severity of allergic response was assessed 45 min after the last induction by measuring changes in body temperature using a rectal thermometer (Bioseb, France) and by evaluating clinical score (0=no symptoms; 1=scratching and rubbing around the nose and head; 2=puffiness around the eyes and mouth, pilar erecti; 3=reduced activity and/or decreased activity with increased respiratory rate; 4=no activity after prodding; and 5=death).

Allergic reactions were observed in sensitized mice after oral challenge and scored. Indeed, a significant decrease in body temperature was induced after PE challenge and MCPT-1 protease, released after mast cell degranulation, was measured in serum of sensitized mice. As expected, PE-specific IgE antibodies were also detected in serum.

The inventors investigated the preventive efficacy of low-dose of IL-2 (Proleukin® (aldesleukin), Novartis 50,000 IU/injection in 200 µL) in this murine allergy model against peanuts. Mice were daily i.p. injected with IL-2 or PBS as control for 5 consecutive days and then sensitized and challenged with PE according to the above protocol.

Results

The inventors observed that IL-2 prevents food allergy since IL-2-treated mice had no clinical symptoms while control mice had pruritis, edema and/or lethargy symptoms (FIG. 7). The protective effect of low-dose IL-2 was confirmed by the absence of changes in body temperature in contrast to sensitized controls.

These results show that IL-2 efficiently prevents peanut allergy reactions in mice model.

The invention claimed is:

1. A method for treating a food allergy in a subject comprising administering Interleukin-2 (IL-2) to said subject, wherein IL-2 is administered: (i) subcutaneously at a dosage of less than 5 MIU/day, (ii) orally at a dosage of between 0.5 and 10 MIU/day or (iii) intranasally at a dosage of between 0.5 and 5 MIU/day.

2. The method of claim 1, wherein the subject is afflicted with a food allergy selected from the group consisting of peanut allergy, milk allergy, nut allergy, corn allergy, fruit allergy, garlic allergy, oat allergy, shellfish allergy, soy allergy, wheat allergy, egg allergy, sesame allergy, olive oil allergy, cheese allergy, crustacean allergy, and fish allergy.

3. The method of claim 2, wherein the wheat allergy is gluten allergy.

4. The method of claim 1, wherein IL-2 is administered repeatedly.

5. The method of claim 1, wherein IL-2 is administered during a cyclic period that lasts from about 1 month to about one year, said cyclic period being optionally repeated every two or three years.

6. The method of claim 1, wherein said method reduces the risk, severity or occurrence of an allergic response or crisis.

7. The method of claim 1, wherein IL-2 is administered in combination with a food allergen.

8. The method of claim 2, wherein the subject is afflicted with an egg allergy.

9. The method of claim 1, wherein IL-2 is administered subcutaneously at a dosage of less than 5 MIU/day.

10. The method of claim 9, wherein IL-2 is administered subcutaneously at a dosage of less than 3.5 MIU/day.

11. The method of claim 10, wherein IL-2 is administered subcutaneously at a dosage of between 0.05 MIU and 2 MIU/day or between 0.1 and 3 MIU/day.

12. The method of claim 1, wherein IL-2 is administered orally at a dosage of between 0.5 and 10 MIU/day.

13. The method of claim 12, wherein IL-2 is administered orally at a dosage of between 1 and 5 MIU/day.

14. The method of claim 12, wherein IL-2 is administered orally at a dosage of between 5 and 10 MIU/day.

15. The method of claim 1, wherein IL-2 is administered intranasally at a dosage of between 0.5 and 5 MIU/day.

16. The method of claim 15, wherein IL-2 is administered intranasally at a dosage of between 1 and 5 MIU/day.

17. A method for treating a food allergy in a subject comprising administering Interleukin-2 (IL-2) to said subject, wherein IL-2 is administered subcutaneously, orally or intranasally at a dosage of 0.05 to 10 MIU/m$^2$/day.

18. The method according to claim 1, wherein IL-2 is aldesleukin.

19. The method according to claim 17, wherein IL-2 is aldesleukin.

* * * * *